United States Patent [19]

Katsuyama et al.

[11] 4,435,362
[45] Mar. 6, 1984

[54] INTEGRAL MULTILAYER ANALYTICAL ELEMENT FOR THE ASSAY OF TOTAL PROTEIN

[75] Inventors: Harumi Katsuyama; Masaaki Terashima, both of Asaka, Japan

[73] Assignee: Fuji Shashin Film Kabushiki Kaisha, Japan

[21] Appl. No.: 441,062

[22] Filed: Nov. 12, 1982

[30] Foreign Application Priority Data

Nov. 17, 1981 [JP] Japan ................................. 56-184080

[51] Int. Cl.³ ...................... G01N 21/78; G01N 33/68
[52] U.S. Cl. ......................................... 422/56; 436/86
[58] Field of Search ............... 422/56, 57, 58; 436/86, 436/87

[56] References Cited

U.S. PATENT DOCUMENTS

| | | | |
|---|---|---|---|
| 3,104,209 | 9/1963 | Scott ................................. | 422/56 X |
| 3,310,382 | 3/1967 | Kingsley ............................... | 436/86 |
| 3,917,452 | 11/1975 | Rittersdorf et al. .............. | 422/56 X |
| 4,132,528 | 1/1979 | Eikenberry et al. .............. | 422/57 X |

*Primary Examiner*—Arnold Turk
*Attorney, Agent, or Firm*—Jacobs & Jacobs

[57] ABSTRACT

An improved integral multilayer analytical element for the assay of total protein contained in liquid sample. The element comprises a transparent support on which a reagent layer and a spreading layer are superposed. The feature of the element exists in the reagent layer comprising potassium sodium tartarate, a cupric salt, a basic compound providing a pH in excess of about 12.0 in the element under conditions of use thereof, an alkali-proof polymer and an alkali metal ion complexing agent.

7 Claims, No Drawings

INTEGRAL MULTILAYER ANALYTICAL ELEMENT FOR THE ASSAY OF TOTAL PROTEIN

BACKGROUND OF THE INVENTION

1. Field of the Invention

This invention relates to an integral multilayer analytical element for the assay of total protein contained in a liquid sample such as blood, serum and urine.

2. Description of the Prior Art

In the past, the determination of the protein content of a liquid sample by means of the biuret reaction has been carried out as a solution assay or wet chemistry technique [see, for example, Sugawara and Soejima, "TANPAKUSHITSU-NO-TEIRYOHO (Determination of Protein)," GAKKAI SYUPPAN CENTER (1977)]. Although the wet chemistry methods are useful, they often require an expensive and complicated equipment, troublesome handling, and a long time for the analysis. As an alternative to the aforementioned wet chemistry assay techniques, a variety of the so-called dry chemistry techniques and equipments therefor have recently been proposed, which make the rapid, simple and low-cost assay possible. For example, U.S. Pat. No. 4,132,528 (which corresponds to Japanese Patent Laid-Open Publication No. 101398/1979) discloses an integral multilayer analytical element for the detection of an analyte in a liquid sample, wherein the element comprises a spreading layer to distribute uniformly the sample spotted thereon and a reagent layer in which the sample is maintained and reacted with a reagent to provide a detectable change, said element being characterized by that the reagent layer contains substantially no sodium ion, an amount of base sufficient to provide a pH in excess of about 12 in said element, and an alkaline protective polymer. In making such dry chemistry analytical element, when a sodium ion is contained in a coating liquid providing the reagent layer, a phase separation is often found in the coating liquid during coating and it is difficult to provide a uniform reagent layer. Moreover, the reagent layer containing a sodium ion has disadvantage that it is highly hygroscopic and so, the element using such reagent layer tends to yellow and the performance of the element is rapidly reduced. It is, therefore, impossible to apply a conventional biuret reagent composition as it is, which can be employed in the solution method of the prior art and which contains sodium ion sources such as Rochelle salt (or potassium sodium tartarate) and sodium hydroxide, to the aforementioned integral analytical element.

The inventors of this invention have studied a stable, integral multilayer analytical element for the assay of total protein, wherein the conventional biuret reagent composition containing a sodium ion can be used. As a result, the inventors have found that such analytical element can be made by adding a specific compound to the reagent layer. This invention has been accomplished on the basis of the discovery described above.

SUMMARY OF THE INVENTION

According to this invention, there is provided an integral multilayer analytical element for the assay of total protein contained in a liquid sample by means of the biuret reaction. The element comprises a transparent support on which a reagent layer and a spreading layer are superposed.

The reagent layer of said element comprises potassium sodium tartarate, a cupric salt, a basic compound providing a pH in excess of about 12.0 in said element under conditions of use thereof, an alkali-proof polymer and an alkali metal ion complexing agent.

A basic structure of the multilayer analytical element of this invention is such one that a transparent support, a reagent layer and sample spreading layer are superposed in this order. The sample spreading layer on which a liquid sample is spotted is located on the top of the element. The spreading layer spreads the liquid sample spotted thereon, then penetrates it therethrough and finally distributes the liquid sample uniformly per unit area in the reagent layer independently of the volume of the applied drop. Such basic structure of the multilayer analytical element of this invention is known as a structure of an analytical element for the simple and quick determination of a specific chemical component contained in a liquid sample by means of dry chemistry methods.

Typical structures of such analytical elements are disclosed in detail, for example, in Japanese Patent Laid-Open Publications Nos. 3488/1977 (U.S. Pat. No. Re. 30267) and 164356/1980 (U.S. Pat. No. 4,292,272), and Clinical Chemistry, Vol. 24, No. 8, 1335 to 1350 (1978).

Potassium sodium tartarate which is used as one component of the biuret composition of the reagent layer of this invention. Potassium sodium tartarate is a complexing agent for a cupric ($Cu^{++}$) ion generally employed in a conventional solution method and it can easily be obtained and inexpensive. If desired, the reagent layer of the analytical element of this invention may include other tartarates such as sodium tartarate, potassium tartarate, ammonium tartarate, or lithium tartarate. Typical cupric salts employed in this invention include aqueous cupric salts such as cupric sulfate, cupric nitrate, cupric chloride, cupric bromide, cupric iodide, cupric acetate and the like. Examples of a basic compound to provide a pH in excess of about 12.0 in the element under conditions of use thereof include sodium hydroxide, potassium hydroxide, lithium hydroxide, calcium hydroxide and the like.

An alakli-proof polymer in the reagent layer of the element of this invention is used to support a biuret reagent composition. Examples of the alkali-proof polymer include agarose, starch, polyvinyl pyrrolidone, polyvinyl pyridine, methylcellulose, methyl hydroxypropyl cellulose, polyvinyl alcohol, copolymer made up by more than one monomer constituting the aforementioned polymer, and polymer blends.

The feature of this invention is the incorporation of an alkali metal ion complexing agent in the reagent layer which comprises a biuret reagent containing a sodium ion source compound and an alkali-proof polymer, so that the stability of the reagent layer is improved, that is, the ability to provide a highly alkaline condition in the reagent layer is maintained for a long time. Useful examples of such alkali metal ion complexing agent include polyalkyleneglycol, cryptates, crown ethers and the like. Typical polyalkyleneglycol are polyethyleneglycol and polypropyleneglycol, preferably having a molecular weight of about 1,000 to about 5,000. Cryptates and crown ethers are described in detail in Ryohei Oda et al. ed. "Kuraun-eteru no Kagaku (Chemistry of Crown ethers)," extra issue No. 74 of Kagaku (Chemistry), 1978. Specific examples of cryptates and crown ethers are 4,13-didecyl-1,7,10,16- tetraoxa-4,13-diazacylooctadacane (e.g. Kryptofix 22 (Registered Trademark) produced by Merck), 1,4,10,-trioxa-7,13-diazacyclopentadecane (e.g. Kryptofix 21 (Registered Trademark) produced by Merck), 1,4,7,10,13-pentaoxacyclopentadecane (15-crown-5), 1,4,7,10,13,16-hexaoxacyclooctadecane (18-crown-6).

An amount of potassium sodium tartarate contained in the reagent layer of the analytical element of this invention is from 10 to 70%, preferably from 20 to 50% on the basis of the weight of the alkali-proof polymer. An amount of a basic compound sufficient to provide a pH in excess of about 12.0 in the element under conditions of use thereof is from 5 to 50%, preferably from 10 to 30% on the basis of the weight of the alkali-proof polymer. An amount of an alkali metal ion complexing agent necessary to keep the reagent layer stable for a long time is from 3 to 100%, preferably 4 to 50% on the basis of the weight of the alkali-proof polymer.

Although the alkali metal ion complexing agent used in this invention is directed to substantially improve the stability of the reagent layer containing a sodium ion, it may also be contained in a reagent layer containing substantially no sodium ion and it may improve the stability of the reagent layer.

The analytical element of this invention may be prepared by various conventional techniques. For example, a transparent support comprising a polymer material such as polyethyleneterephthalate, polycarbonate or polyvinyl compounds, is coated with an aqueous liquid containing a reagent layer composition to give a dry reagent layer of 2 to 50 μm in thickness and then, a spreading layer is provided on the reagent layer. Such spreading layer includes non-fibrous, porous spreading layer such as a membrane filter and a porous layer as disclosed in Japanese Paent Laid-Open Publication No. 53888/1974 and U.S. Pat. No. 3,992,158 wherein polymeric micro beads and glass microbeads are fixed with a hydrophilic binder such as gelatine so as to form void therein; a porous layer having continuous void as disclosed in Japanese Patent Laid-Open Publication No. 90859/1980 (U.S. Pat. No. 4,258,001) wherein non water-swelling organic polymer micro beads are brought into ball-to-ball contact with each other with non water-swelling organic polymer adhesive; or fibrous, porous spreading layer of woven cloth as disclosed in Japanese Patent Laid-Open Publication No. 164356/1980 (U.S. Pat. No. 4,292,272).

The analytical element of this invention may be provided with, if desired, an adhesion layer, a light reflection layer, a filtering layer and the like which may be incorporated into a conventional integral multilayer analytical element.

In the determination of the total proteins contained in a sample liquid using the analytical element of this invention, the sample liquid of 3 to 50 μl, preferably 7 to 20 μl is spotted on the spreading layer of the element, and then the element is, if necessary, incubated at 30° C. to 50° C., preferably 35° C. to 40° C. for 1 to 2 minutes, preferably 1 to 10 minutes, after which a detectable change produced in the element is measured as a refelction density of a light transmitted through a filter which permits a light of suitable wavelength of 500 to 650 nm to transmit therethrough, from the transparent support side of the element. The total content of proteins may be obtained from a calibration curve. Alternatively, semiquantitative analysis may be carried out by visual comparison of the color change in the element with a standard color previously prepared.

This invention will now be described in detail with reference to the following Examples.

EXAMPLE 1

Sodium hydroxide (1.35 g, 0.03 mole), lithium hydroxide (1.42 g, 0.03 mole), and Rochelle salt (potassium sodium tartarate, 4.5 g, 0.02 mole) were dissolved in 30 ml of water. Cupric sulfate penta hydrate ($CuSO_4.5H_2O$, 3.24 g) dissolved in 20 ml of water was added to the above Rochelle salt/base solution with stirring to prepare a biuret reagent solution.

A polymer solution (60 g) of 20% polyvinyl pyrrolidone K-90 (Average M.W. 700,000) aqueous solution to which polyethyleneglycol (Average M.W. 1500) was added, was added to and mixed with the biuret reagent solution with stirring. Polyethyleneglycol was used in an amount of from 0 to 4% on the basis of the weight of polyvinyl pyrrolidone used. p-Nonylphenoxy polyglycidol (1 g) was added thereto to prepare a coating liquid for a reagent layer.

A transparent support of 180 μm thick polyethyleneterephthalate film was precoated with a solution containing nitrocellulose and gelatine. The hydrophilic support thus obtained was coated with the coating liquid using a knife edge coater to give 30 μm dry thick coating.

The reagent layer thus prepared was swollen with water and then, a cotton broadcloth (#100) was pressed on the swollen reagent layer and dried to prepare an integral multilayer analytical element for the assay of total protein.

COMPARATIVE EXAMPLE 1

The procedure of Example 1 was repeated to prepare an integral multilayer analytical element, except that lithium hydroxide (4.2 g, 0.10 mole), tartaric acid (2.4 g, 0.02 mole) and cupric sulfate penta hydrate ($CuSO_4.5H_2O$, 3.24 g) were used to prepare a biuret reagent solution and a polymer solution to which no polyethyleneglycol was added, was used.

Evaluation Test

Integral multilayer analytical elements for the determination of total protein were evaluated as follows: Each 10 μl of 7 g/dl albumin solution in physiologic saline was spotted onto the element and then the element was incubated at 37° C. for 5 minutes. Then, the element was evaluated colorimetrically by monitoring the change in reflection density of a light transmitted through a 550 nm interference filter from the transparent support side of the element.

A color development ratio is defined as a ratio of a reflection density of the element which was left to stand at 35° C. and 40% of relative humidity, for a predetermined period of time, to a reflection density of the element just after the preparation of the element. The results are given in the following Table.

|  | Polyethyleneglycol Content (%) | Color Development Ratio after 7 days (%) |
|---|---|---|
| Example 1-A | 1 | 79 |
| Example 1-B | 2 | 83 |
| Example 1-C | 3 | 88 |
| Example 1-D | 4 | 89 |
| Control | 0 | 66 |
| Comparative Example | 0 | 80 |

EXAMPLE 2

The procedure of Example 1 was repeated to prepare an integral multilayer analytical element of the determination of total protein, except that lithium hydroxide (2.84 g) was added as base and polyvinyl pyrrolidone containing 4% polyethyleneglycol (average M.W. 2,000) was used.

The analytical element was left to stand at 35° C. and 40% of relative humidity for one month, after which a color development ratio of the analytical element was 97%. After the storage at 35° C. in the presence of a drying agent for one month, a color development ratio thereof was 100%.

An aqueous solution (10 μl) of protein (albumin) was spotted onto the element which was then evaluated according to the evaluation test described above.

| Protein Content (g/dl) | Reflection Density (550 nm) |
| --- | --- |
| 0 | 0.401 |
| 6.3 | 0.480 |
| 12 | 0.530 |
| 25 | 0.635 |
| 50 | 0.820 |
| 75 | 0.915 |
| 100 | 0.994 |

EXAMPLE 3

The procedure of Example 1 was repeated to prepare an integral multilayer analytical element for the determination of total protein, except that 15-crown-5 was used instead of polyethyleneglycol in an amount of 40% of the weight of polymer used.

A color development ratio of the element was 90%, after it was left to stand at 35° C. and 40% of relative humidity for one month.

What we claim is:

1. An integral multilayer analytical element for the assay of total protein contained in liquid sample using a biuret reaction, said element comprising a transparent support on which a reagent layer and a spreading layer are superposed, said reagent layer being positioned between said spreading layer and said transparent support;

said reagent layer containing potassium sodium tartarate, a cupric salt, a basic compound providing a pH in excess of about 12.0 in said element under conditions of use thereof, an alkali-proof polymer and an alkali metal ion complexing agent.

2. The analytical element according to claim 1, wherein said alkali metal ion complexing agent is selected from the group consisting of polyalkyleneglycol, cryptates and crown ethers.

3. The analytical element according to claim 1, wherein said alkali-proof polymer is selected from the group consisting of agarose, starch, polyvinyl pyrrolidone, polyvinyl pyridine, methylcellulose, methyl hydroxypropyl cellulose, and polyvinyl alcohol.

4. The analytical element according to claim 1, wherein said alkali metal complexing agent is polyethyleneglycol or polypropylene glycol of a molecular weight from about 1,000 to about 5,000.

5. The analytical element according to claim 1, wherein said alkali metal complexing agent is 4,13-didecyl-1,7,10,16-tetraoxa-4,13-diazacyclooctadecane or 1,4,10-trioxa-7,13-diazacyclopentadecane.

6. The analytical element according to claim 1, wherein said alkaly metal complexing atent is 1,4,7,10,13-pentaoxycyclopentadecane or 1,4,7,10,13,16-hexaoxacyclooctadecane.

7. The analytical element according to claim 1, wherein said potassium sodium tartarate is in an amount of from 10 to 70%, by weight of said alkali-proof polymer, said basic compound is in an amount of from 5 to 50% by weight of said alkali-proof polymer and said alkali metal complexing agent is in an amount of 3 to 100% by weight of said alkali-proof polymer.

* * * * *